US00PP36926P2

(12) United States Plant Patent
Hansen

(10) Patent No.: US PP36,926 P2
(45) Date of Patent: Sep. 2, 2025

(54) ***HOSTA* PLANT NAMED 'Humungousaurus'**

(50) Latin Name: ***Hosta* hybrid (Tratt.)**
Varietal Denomination: Humungousaurus

(71) Applicant: Hans A Hansen, Zeeland, MI (US)

(72) Inventor: Hans A Hansen, Zeeland, MI (US)

(73) Assignee: Walters Gardens, Inc., Zeeland, MI (US)

( * ) Notice: Subject to any disclaimer, the term of this patent is extended or adjusted under 35 U.S.C. 154(b) by 0 days.

(21) Appl. No.: 18/831,379

(22) Filed: Dec. 20, 2024

(51) Int. Cl.
*A01H 5/12* (2018.01)
*A01H 6/12* (2018.01)

(52) U.S. Cl.
USPC ..... Plt./353

(58) Field of Classification Search
USPC ..... Plt./353
See application file for complete search history.

*Primary Examiner* — Susan McCormick Ewoldt

(57) ABSTRACT

A new and distinct *Hosta* plant named 'Humungousaurus' with giant, round-mounded habit with very large ovate foliage of heavy substance, with golden yellow color, and deeply impressed veins. Flowers are very pale purple for about three weeks beginning in late June. Scapes are drooping outwardly and holding flowers just above foliage.

2 Drawing Sheets

Latin name and variety denomination of the plant: Botanical classification: *Hosta* hybrid (Tratt.). Variety denomination: 'Humungousaurus'.

STATEMENT REGARDING PRIOR DISCLOSURES UNDER 37 CFR 1.77 (b) (6)

*Hosta* 'Humungousaurus' was first introduced by the inventor as a non-enabling description through the International Cultivar Registration Authority registration in early 2024. No plants of *Hosta* 'Humungousaurus' have been sold in this country or anywhere in the world, nor has any disclosure of the new plant been made, more than one year prior the filing date of this application.

BACKGROUND AND ORIGIN OF THE PLANT

The present invention relates to a new and distinct hosta plant, *Hosta* 'Humungousaurus' hereinafter also referred to as the new plant or just the cultivar name, 'Humungousaurus'. *Hosta* 'Humungousaurus' was hybridized by the inventor as a cross between 'Key West' (not patented) as the female and 'Viking Ship' (not patented) at a wholesale nursery greenhouse in Zeeland, Michigan, USA on Jul. 1, 2015. The seeds were harvested in the autumn of 2015 and sown in February of 2016. The new plant was given the breeder code 15-58-2 in the evaluation process.

The new plant has been asexually propagated by division at the same nursery in Zeeland, Michigan, USA since 2022 and also by careful shoot tip tissue culture with the resultant asexually propagated plants having retained all the same traits as the original plant. *Hosta* 'Humungousaurus' is stable and reproduces true to type in successive generations of asexual reproduction.

No plants of *Hosta* 'Humungousaurus' have been sold, under this or any other name, in this country or anywhere in the world, prior to the filing of this application, nor has any disclosure of the new plant been made prior to the filing of this application with the exception of that which may have been disclosed within one year of the filing date of this application and was either derived directly or indirectly from the inventor.

BRIEF SUMMARY OF THE PLANT

There are over 7,000 registered hosta cultivars with The American Hosta Society, which is the International Cultivar Registration Authority for the genus *Hosta* along with a similar number of unregistered cultivars. The nearest comparison varieties known to the inventor are *Hosta* 'Abiqua Recluse' (not patented), 'Age of Gold' U.S. Plant Pat. No. 30,902, 'Coast to Coast' U.S. Plant Pat. No. 26,469, 'Dancing on the Sun' U.S. Plant Pat. No. 35,944, 'Echo the Sun' U.S. Plant Pat. No. 35,943, 'Fort Knox' (not patented), 'Golden Sculpture' (not patented), 'Piedmont Gold' (not patented), 'Seasons in the Sun' U.S. Plant Pat. No. 34,284, and 'Key West' (not patented).

'Abiqua Recluse' has a slightly smaller habit with smaller leaves of lighter golden with more dimpling between the veins, and the flower scapes are more upright. 'Coast to Coast' is a smaller plant with smaller foliage and slightly shorter scapes. 'Dancing on the Sun' has a smaller habit with smaller leaves that have a more sinuate margin and the flower season is later. 'Echo the Sun' has a significantly smaller habit with smaller foliage that has a more sinuate margin and shorter scapes about one to two weeks later. 'Fort Knox' has a much smaller habit with much smaller foliage that develops fewer veins that are less impressed. 'Golden Sculpture' has more rounded and bullate foliage. 'Piedmont Gold' has more rounded and more bullate that is also has slightly wavy margins, and more downward arching of the leaf blades. 'Seasons in the Sun' is also smaller in habit with smaller more rounded foliage and flowers that stand out well above the foliage.

Comparison with the female parent, 'Key West', has a smaller habit and foliage size, the leaves are more chartreuse, and the scape is more upright. The male parent, 'Viking Ship', has a smaller habit, the foliage is glaucous, bluish-green, bullate with cuspidate apex, and the scapes are more upright.

Other *Hosta* cultivars have chartreuse to golden foliage, but 'Humungousaurus' is distinct from the above mentioned hostas and all other cultivars known to the discoverer by the following combined traits:

1. Giant round-mounded plant;
2. Very large ovate foliage with heavy substance;
3. Foliage color is golden yellow with deeply impressed veins;
4. Very pale purple flowers just above foliage effective for about three weeks beginning in late June;

BRIEF DESCRIPTION OF THE DRAWINGS

The photographs of *Hosta* 'Humungousaurus' demonstrate the overall appearance of the plant, including the unique traits. The colors are as accurate as reasonably possible with color reproductions. Ambient light spectrum, temperature, source and direction may cause the appearance of minor variation in color.

DETAILED BOTANICAL DESCRIPTION

Figure 1:
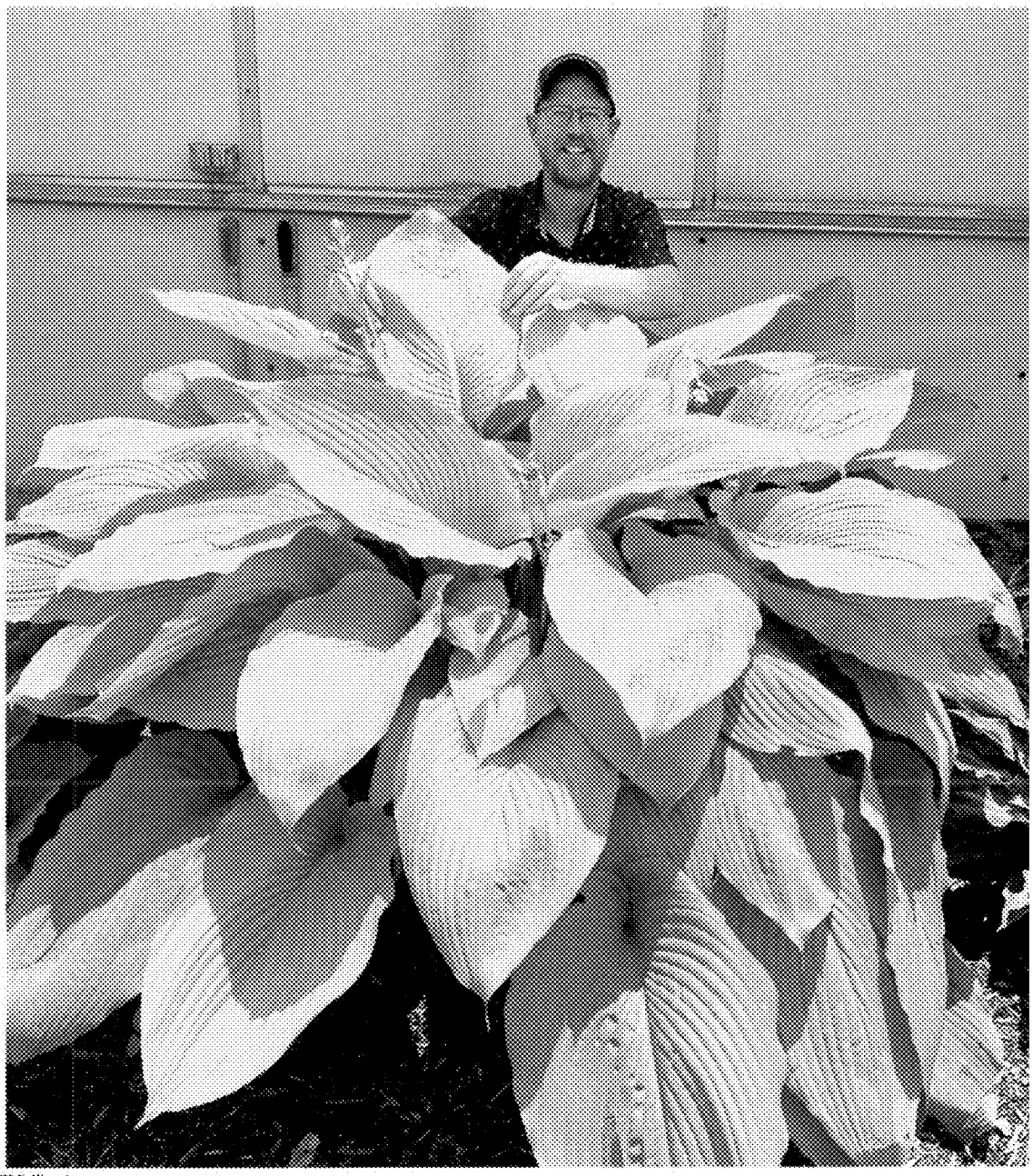
FIG. 1 shows a nine-year-old plant grown in a shaded trial garden just prior to flowering.
Figure 2:
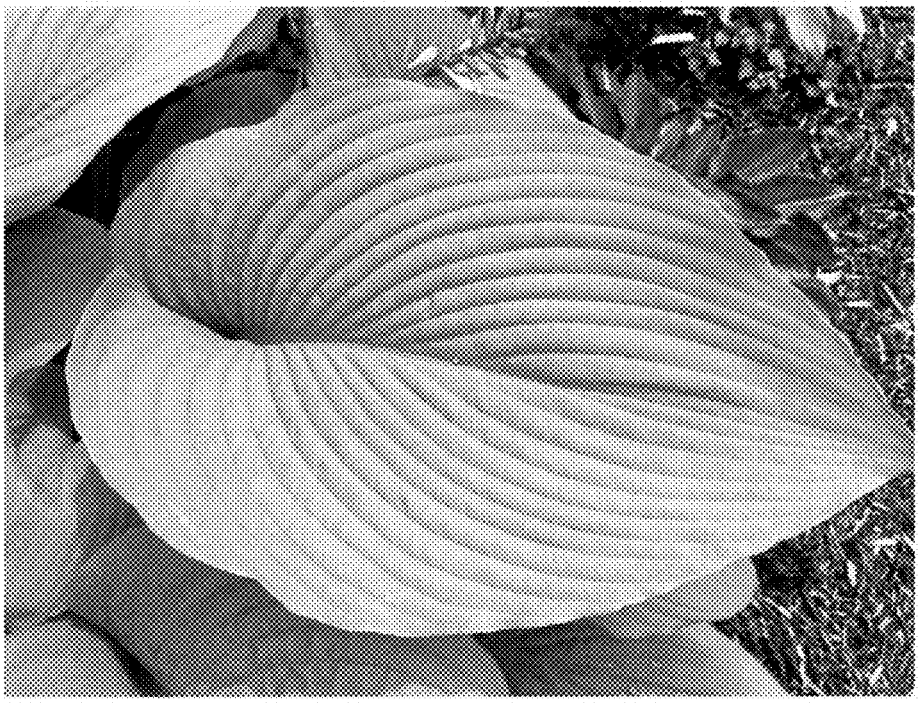
FIG. 2 shows a close-up of a leaf.
Figure 3:
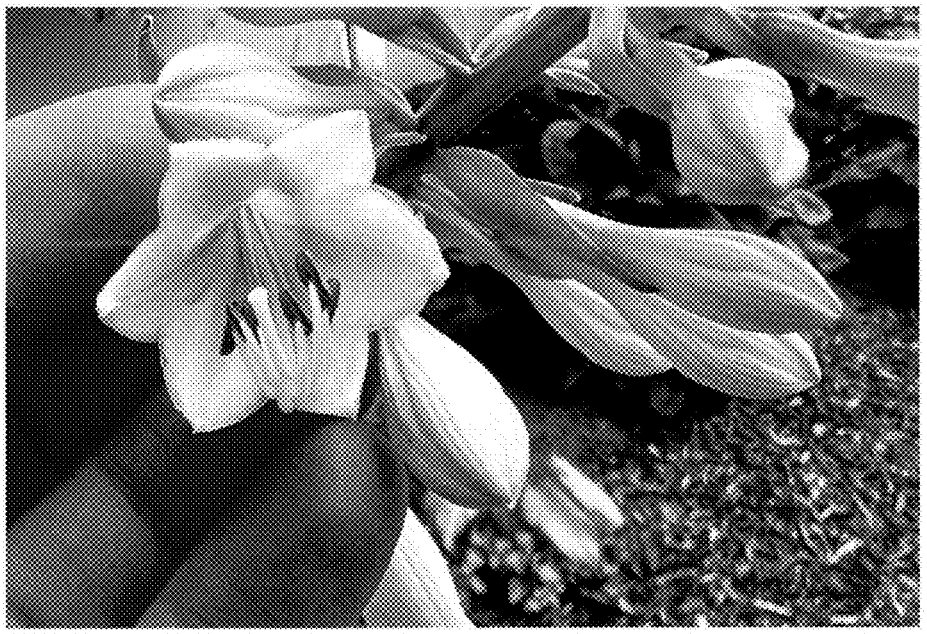
FIG. 3 shows a close-up of the flower scape showing flowers, buds, and foliar bracts.

The following descriptions and color references are based on the 2015 edition of The Royal Horticultural Society Colour Chart except where common dictionary terms are used. The new plant, *Hosta* 'Humungousaurus', has not been observed under all possible environments.

The phenotype may vary slightly with different environmental conditions, such as temperature, light, fertility, moisture and maturity levels, but without any change in the genotype. The following observations and size descriptions are of a nine-year-old plant in a shaded greenhouse in Zeeland, Michigan with supplemental water and fertilizer.

Botanical classification: *Hosta* hybrid;

Parentage: Female or seed parent is 'Key West'; male or pollen parent is 'Viking Ship';

Propagation: Garden division and sterile shoot-tip tissue culture;

Time to initiate roots from tissue culture: About two to three weeks;

Growth rate: Rapid;

Crop time: About 10 to 12 weeks to finish during the summer in a one-liter container from rooted tissue culture plantlet;

Rooting habit: Normal, fleshy, lightly branching;

Plant shape and habit: Hardy herbaceous perennial with basal rosette of leaves emerging from rhizomes producing a large symmetrical rounded-mound of leaves;

Plant size: Foliage height about 109 cm above soil line to the top of the leaves and about 224 cm wide at the widest point slightly above the soil line; about 120 cm to top flowers;

Foliage description: Broadly ovate; acute apex; cordate base; glabrous; matte adaxial; lightly glaucous abaxial; margin entire and faintly undulate; not bullate;

Leaf blade size: To about 48 cm long and 33 cm wide, average about 44 cm long and 31 cm wide;

Leaf blade color: Variable with season and light exposure; early season and shortly after emerging adaxial nearest blend between RHS N144D and RHS 144A; early season and shortly after emerging abaxial between RHS 145A and RHS N144D; mid-season and later summer adaxial some regions with more light between RHS 153D and RHS 160A, others in more shade or beneath another leaf between RHS 146D and 145A; mid-season and later abaxial blend between RHS 151C and RHS N144A with higher light exposure and between RHS 146D and RHS N144D in more shaded leaf portions;

Petiole: Entire; glabrous; glaucous abaxial and matte adaxial; concavo-convex; outwardly from base of plant to leaf base, stiff; to about 63.5 cm long and at base 29 mm across and 17 mm deep; average 59 cm long and base 20 mm wide and 14 mm deep;

Petiole color: adaxial between RHS 146D and RHS 138B; abaxial midrib between RHS 145C and RHS 145D and side portions between RHS 146D and RHS 145A;

Veins: Parallel; moderately impressed adaxial, moderately ribbed abaxial; 15 to 18 pairs with one midrib, average 17 pairs;

Veins color: Emerging adaxial nearest RHS 145C and abaxial nearest RHS 148C; mature adaxial nearest RHS 146B and abaxial nearest RHS 194C;

Flower description- Buds one day prior to opening: Clavate with rounded apex and narrow tubular base; about 58 mm long, apical bulb about 12 mm diameter and tube about 3 mm diameter;

Bud color: One day prior to opening nearest RHS 85D;

Inflorescence: Average flowering portion 39 cm long and 9 cm wide;

Flowers: Perfect; single; campanulate, funnelform; actinomorphic; attitude slightly drooping; about 2.8 cm wide and 63 mm long; narrowed tube portion about 19 mm long and 3.5 mm diameter (distal flowers smaller); persistent; effective for a normal period, usually one day on plant or as cut flower; scapes remain effective with flowers beginning early summer for about three weeks; about 60 flowers per scape; average spacing between flowers about 0.5 cm, significantly greater in proximal flowers;

Floral bracts: Lanceolate; acute apex; truncate sessile base; concavo-convex; persistent; drying and dehiscing with seed maturing; to about 72 mm long and 15 mm wide, decreasing distally;

Floral bract color: Upon anthesis between RHS 146D and RHS 145A with a slight blush of between RHS N187B and RHS 187B abaxial and adaxial;

Flower fragrance: None detected;

Corolla size: To about 63 mm long and 28 mm wide; tube portion about 20 mm long and 3.5 mm diameter, flared bulb portion about 43 mm long and 28 mm wide;

Tepal: Six; two nearly identical sets of three, glabrous, entire; acute apex; fused in basal 38 mm; inner set with translucent margin about 1.5 mm wide; approximately 63 mm long and about 13 mm wide;

Tepal color: Coloring of both sets adaxial longitudinal center about 4 mm wide between RHS 84D and RHS 76C longitudinal edge nearest RHS NN155D without obvious veins; abaxial blend between RHS NN155D and RHS 85D; abaxial tube blend between RHS NN155D and RHS 85D;

Gynoecium: Single; tri-carpelled;

*Style*.—Single, approximately 69 mm long, 1.0 mm diameter, curved upward about 90° in distal 5 mm; color nearest RHS 155A.

*Stigma*.—Globose, about 1.5 mm in diameter; color nearest RHS NN155A.

*Ovary*.—Ellipsoidal; longitudinally fluted, about 7 mm long and 3 mm diameter at widest; rounded apex and truncate base; color nearest RHS 145A.

Androecium:

*Filaments*.—Six, approximately 65 mm long and 0.7 mm in diameter; curved upward in the apical 10 mm; color nearest RHS 145D proximally and nearest RHS 155A distally.

*Anthers*.—Elliptic; dorsifixed, longitudinally dehiscent; about 4 mm long and 1 mm wide; color nearest RHS 163C.

*Pollen*.—Abundant; globose; less than 0.1 mm diameter; color nearest RHS 17B.

Peduncle: Usually one per mature division; glaucous, glabrous to becoming slightly lustrous later in season; aspect drooping outwardly; about 105 cm long, and to about 9 mm in diameter at base; average about 100 cm tall and about 8 mm diameter at base;

Peduncle color: When flowering proximal potion below foliage nearest RHS 145C, distally nearest RHS 146C with moderate blush or maculate with nearest RHS 187C;

Pedicel: Glabrous; glaucous; terete; secund; to 18 mm long and 2 mm diameter, average about 12 mm long and 1.5 mm diameter; aspect slightly drooping; color nearest blend of nearest RHS 194D and RHS 76C;

Fruit: Tri-valved dehiscent capsule; oblong elliptic, about 33 mm long and 8 mm diameter, with thin beak about 0.5 mm diameter extending about 0.5 mm; color as maturing nearest RHS 138A and in maturity nearest RHS 161B;

Seed: Typically about 46 per capsule; endospermic; flattened-elliptic wing surrounding embryo situated toward one end of ellipse; up to about 12 mm long and 3.5 mm wide and 1 mm thick at embryo; color nearest RHS 202A;

Disease tolerance and resistance: The new plant has not shown any resistance to pests and diseases common to hostas. The plant grows best and shows best coloration with plenty of moisture, adequate drainage and light sun, but is able to tolerate some drought when mature. Hardiness at least from USDA zone 3 through 9, and other disease resistance is typical of that of other hostas.

It is claimed:

1. A new and distinct ornamental plant cultivar named *Hosta* 'Humungousaurus' as herein described and illustrated.

* * * * *